(12) United States Patent
Kysilka et al.

(10) Patent No.: US 8,513,460 B2
(45) Date of Patent: Aug. 20, 2013

(54) PROCESS FOR PREPARING N-(HYDROCARBYL) PHOSPHORIC OR THIOPHOSPHORIC TRIAMIDES

(75) Inventors: Vladimir Kysilka, Brno (CS); Jiri Kopenec, Prague (CS); Jiri Krepelka, Kralupy nad Vltavou (CS)

(73) Assignee: Agra Group, A.S., Strelske Hostice (CZ)

( * ) Notice: Subject to any disclaimer, the term of this patent is extended or adjusted under 35 U.S.C. 154(b) by 195 days.

(21) Appl. No.: 13/123,062

(22) PCT Filed: Sep. 30, 2009

(86) PCT No.: PCT/CZ2009/000114
§ 371 (c)(1),
(2), (4) Date: Apr. 7, 2011

(87) PCT Pub. No.: WO2010/045895
PCT Pub. Date: Apr. 29, 2010

(65) Prior Publication Data
US 2011/0196172 A1    Aug. 11, 2011

(30) Foreign Application Priority Data
Oct. 20, 2008  (CV) .................................. 2008-638

(51) Int. Cl.
*C07F 9/06*    (2006.01)
(52) U.S. Cl.
USPC ............................................... 564/14

(58) Field of Classification Search
USPC ............................................... 564/14
See application file for complete search history.

(56) References Cited

U.S. PATENT DOCUMENTS

| 4,530,714 | A | 7/1985 | Kolc et al. |
| 5,770,771 | A | 6/1998 | Sulzer et al. |
| 5,872,293 | A | 2/1999 | Sulzer et al. |
| 5,883,297 | A | 3/1999 | Sulzer et al. |
| 5,955,630 | A | 9/1999 | Cheng et al. |

FOREIGN PATENT DOCUMENTS
WO    WO 2007/054392    5/2007

OTHER PUBLICATIONS

National Industrial Chemicals Notification & Assessment Scheme, Full Public Report, Worksafe Australia, File No. NA/467, Jan. 1997.

*Primary Examiner* — Peter G O Sullivan
(74) *Attorney, Agent, or Firm* — Notaro, Michalos & Zaccaria P.C.

(57) ABSTRACT

The invention provides a process for preparing N-(hydrocarbyl)phosphoric or thiophosphoric triamides with substantially improved yields and purity. Two equivalents of hydrocarbylamine are used in the reaction with phosphoryl or thiophosphoryl chloride and then with ammonia in an aromatic solvent. The invention further relates to N-(hydrocarbyl)phosphopric or thiophosphoric triamides having the purity of at least 98% wherein R is a hydrocarbyl group and X is O or S.

$$(RNH)(NH_2)_2P=X \qquad (I).$$

8 Claims, No Drawings

PROCESS FOR PREPARING N-(HYDROCARBYL) PHOSPHORIC OR THIOPHOSPHORIC TRIAMIDES

FIELD OF THE INVENTION

The invention relates to a process for preparing N-(hydrocarbyl)phosphoric or thiophosphoric triamides with substantially improved yields and purity. These compounds have interesting biological activities.

BACKGROUND ART

N-(hydrocarbyl)phosphoric or thiophosphoric triamides, their preparation and their interesting biological activity were first described in the document U.S. Pat. No. 4,530,714. They were proposed for different industrial applications, e.g. in urea-containing fertilizers to improve nitrogen utilization. There is a great demand for a process for preparing N-(hydrocarbyl)phosphoric or thiophosphoric triamides in a cost-effective and environmentally friendly way. The term "hydrocarbyl" as used herein represents alkyl or aryl groups.

N-(hydrocarbyl)phosphoric or thiophosphoric triamides are generally prepared by a two-step procedure. An intermediate N-(alkyl- or aryl)amidephosphoryl or thiophosphoryl dichloride is prepared from phosphoryl- or thiophosphoryl chloride and the corresponding hydrocarbylamine in the first step. N-(hydrocarbyl)phosphoric or thiophosphoric triamide is then prepared by the reaction of N-(alkyl- or aryl)amidephosphoryl or thiophosphoryl dichloride with ammonia in the second step. A typical representative of this group of compounds is N-(n-butyl)thiophosphoric triamide (hereinafter referred to as NBPT), the preparation of which is the object of the present invention.

U.S. Pat. No. 4,530,714 describes the preparation of N(n-butyl)amidethiophosphoryl dichloride (hereinafter abbreviated NBTDC) by the reaction of n-BuNH$_3$Cl with 5 equivalents of thiophosphoryl chloride, 72 hours at 135° C. NBTDC is then separated from the resulting mixture by a vacuum distillation, 105-112° C., 0.75 torr. The yield of NBTDC was not mentioned there. This process is not suitable for an industrial use and thus, several improvements of this step were proposed. U.S. Pat. No. 5,770,771 describes a continuous process for the preparation of NBTDC by the reaction of thiophosphoryl chloride, n-butylamine and triethylamine, in approx. equimolar ratios, in tetrahydrofurane as the preferred solvent. The resulting mixture is a complex homogeneous phase. WO 2007/054392 A1 describes the preparation of NBTDC by the reaction of thiophosphoryl chloride, n-butylamine and low volatile tertiary amine, preferably tributylamine, in approx. equimolar ratios, in ethylacetate as the preferred solvent. The resulting mixture is a complex homogeneous phase. The above mentioned processes have serious drawbacks. There is an expert prejudice that the used inert trialkylamine exclusively binds HCl generated from the reaction in the first step. However, HCl can also react with the free n-BuNH$_2$ present in the solution to form inert n-BuNH$_3$Cl, which leads to a decreased conversion of phosphoryl chloride and to a longer reaction time of this step. The intermediate and all side products are in the form of a complex homogeneous phase that comprises NBTDC, the starting thiophosphoryl chloride, triethylammonium or tributylammonium chloride and their free bases, tetrahydrofurane or ethylacetate and side phospho-products. Vacuum distillation of NBTDC is necessary when a better purity of NBTDC is required.

The final product NBPT is prepared from NBTDC and ammonia in the second step. U.S. Pat. No. 5,770,771 describes a continuous process for the preparation of NBPT by the reaction of NBTDC in the form of a complex homogeneous phase obtained in the first step with a large excess of ammonia at about 0° C. in the second step. U.S. Pat. No. 5,883,297 describes a similar process for preparing NBPT starting directly from the NBTDC intermediate. WO 2007/054392 describes a method of preparing NBPT by the reaction of NBTDC in the form of a complex homogeneous phase obtained in the first step with a moderate excess of ammonia (5-6-fold excess) at 0° C. in the second step. The above mentioned processes for preparing NBPT have several drawbacks, too. The resulting NBPT prepared according to the state-of-art documents is in the form of a very complex heterogeneous and odoriferous mixture, which comprises, besides NBPT, a substantial amount of ammonium chloride and ammonia, trialkylammonium chloride and its free base, non-substituted thiophosphoric triamide, tetrahydrofurane or ethylacetate and side phospho-products. The separation of NBPT from ammonium chloride and the removal of all side odoriferous products and solvents from the complex mixture is a very tough technological and environmental problem. The purity of the resulting NBPT mentioned in the U.S. Pat. No. 5,770,771 is 92.4 and 93.4 wt. %.

U.S. Pat. No. 5,872,293 teaches the use of at least 16-fold molar excess of ammonia in the second step of the preparation of NBPT to enable the removal of the main portion of ammonium chloride from the reaction mixture in the form of a separable ammonium liquid phase. However, the proposed re-cyclation of this phase should not be repeated too many times, because of the accumulation of the impurities, thus, further treatment of this ammonium phase remains a big ecological problem. Crude NBPT is separated from the remaining liquid phase by vacuum distillation, but the product is not stable at these conditions. A stirred film vacuum evaporation is protected in U.S. Pat. No. 5,955,630 to avoid the degradation of the product. A further treatment or a method for disposal of the odoriferous distilled phase were not described there. Yields and purity of NBPT are low and further purification of NBPT is necessary. WO 2007/054392 describes an improved separation of ammonium chloride and subsequently NBPT from the complex heterogeneous phase by addition of water. The water phase with ammonium chloride is separated from the organic phase. Ethylacetate is then distilled off by vacuum distillation from the organic phase, so that low volatile tributylamine phase and product phase are formed, the product phase is then separated. Hot water is added to the product phase and NBPT is then precipitated by cooling. The improved yield of NBPT was 66% with the purity of 76 wt. %. However, such quality of NBPT is still not sufficient for an agricultural use, because the purity of NBPT of at least 85 wt. % was approved for such applications, as taught in the document "N-(n-butyl)thiophosphoric triamide", National Industrial Chemicals Notification and Assessment Scheme (Full Public Report), Worksafe Australia, File No.: NA/467, January 1997.

Related N-(hydrocarbyl)phosphoric or thiophosphoric triamides can be prepared in a similar way to NBPT.

There are many drawbacks in preparing N-(hydrocarbyl)phosphoric or thiophosphoric triamides according to the above mentioned prior art. The separation of ammonium chloride from the product is ineffective. Large volumes of odoriferous wastes in the liquid form are economic and ecological problem. Vacuum distillation is necessary to separate the product, side products, solvent and trialkylamine from the complex heterogeneous phase. The described processes for preparing N-(hydrocarbyl)phosphoric or thiophosphoric triamides are technologically and environmentally demanding and result in low yields and low purities of the product. A repeated purification procedure is necessary to obtain the quality of the product required for an industrial use.

As follows from the above mentioned prior art, there is still a great demand for an effective and ecological process for preparing N-(hydrocarbyl)phosphoric or thiophosphoric triamides.

The technical problem underlying the present invention is therefore to provide a process for preparing N-(hydrocarbyl) phosphoric or thiophosphoric triamides with substantially improved yields and purity by a simpler and more ecological process.

DISCLOSURE OF THE INVENTION

The present invention solves the above-identified technical problem by providing a process for preparing N-(hydrocarbyl)phosphoric or thiophosphoric triamides of general formula I $$(RNH)(NH_2)_2P=X \qquad (I)$$

wherein R is a hydrocarbyl group and X is O or S, comprising the following steps:
a) reacting about one equivalent of $Cl_3P=X$, wherein X is O or S, with about two equivalents of hydrocarbylamine in an aromatic solvent, preferably toluene, to obtain a solution of compound of general formula II $$(RNH)Cl_2P=X \qquad (II)$$

wherein R and X are as defined above, and a solid phase containing hydrocarbylammonium chloride,
b) removing the solid phase to obtain the solution,
c) adding at least four equivalents of ammonia to the solution obtained in step b) to obtain a suspension of solid N-(hydrocarbyl)phosphoric or thiophosphoric triamide of the general formula I and solid ammonium chloride in the aromatic solvent,
d) heating the suspension obtained in step c) to the temperature in the range of from 50 to 80° C. to obtain a solution of N-(hydrocarbyl)phosphoric or thiophosphoric triamide of the general formula I and a solid phase containing ammonium chloride,
e) removing the solid phase at the temperature in the range of from 50 to 80° C. to obtain the solution,
f) cooling the solution obtained in step e) to the temperature in the range of from 0 to 25° C. to obtain solid N-(hydrocarbyl)phosphoric or thiophosphoric triamide of the general formula I.

The hydrocarbyl group typically contains up to 20 carbon atoms. It is preferably selected from the group comprising $C_1$ to $C_{18}$ alkyl, $C_6$ to $C_{10}$ cycloalkyl and $C_6$ to $C_{12}$ aryl. The hydrocarbyl group may optionally be substituted with groups such as halogen, $C_1$-$C_6$ alkoxy, $C_1$-$C_6$ alkylthio, nitro, cyano, dialkylamino. The hydrocarbyl group can also be substituted with protected hydroxy or mercapto group, the protecting group being any commonly used protecting group, such as trimethylsilyl or tetrahydropyranyl group.

In step a), the molar ratio of the reagents is about one equivalent of $Cl_3P=X$ to about two equivalents of hydrocarbylamine, which shall mean the molar ratio of 1:2±10%.

The step a) according to the present invention is very quick and selective. One equivalent of hydrocarbylamine forms monoamide of phosphoryl or thiophosphoryl chloride in a high purity and yield, and moreover, this intermediate is soluble in the aromatic phase. The second equivalent of hydrocarbylamine forms the corresponding hydrocarbylammonium chloride which is insoluble in the aromatic phase and is thus easily separated by filtration. Corresponding free amines can be obtained from the separated hydrocarbylammonium chloride by treatment with alkali metal hydroxide and then re-used in step a). The reaction is exothermic, thus, moderate cooling of the reaction mixture is necessary. The reaction can be carried out in a broad temperature range of from 0° C. to 50° C. without any impact on the yield and purity of the monoamide intermediate.

The step b) is smooth, because the solid phase is coarse enough to be easily filtered off. The filtration cake of ammonium salt can be washed with aromatic solvent.

The step c) is quick and selective. At least four equivalents of ammonia are necessary both for the conversion of monoamide of phosphoryl or thiophosphoryl chloride to the corresponding triamide and for the removal of the generated hydrogen chloride in the form of ammonium chloride. The reaction rate depends mainly on the rate of adding ammonia and on its concentration. The inconvenience of the low solubility of ammonia can be overcome either by continuously adding gaseous ammonia or by repeatedly adding small portions of liquid ammonia to the reaction mixture at a low temperature, preferably about 0° C. or less. The use of a pressure vessel in the step c) is favorable, for about two bars of ammonia overpressure are beneficial for a good reaction rate of the step c). The reaction is finished after the termination of ammonia consumption. The temperature range of from −20° C. to 25° C. is favorable in this step. The resulting mixture comprises the solid product of the general formula I, solid ammonium chloride and the liquid phase in which small amounts of side phospho-products formed in the reaction are dissolved.

The step d) consists in heating of the resulting mixture from the step c) to the temperature in the range of from about 50 to about 80° C. The product is dissolved under these conditions, while ammonium chloride remains in the solid state. We have found that the product is sufficiently stable during this operation.

The step e) is smooth, because the solid phase of ammonium chloride is easily filtered off. The filtration cake can be washed with hot aromatic solvent.

The step f) consists in cooling the hot filtrate to the temperature in the range of from 0 to 25° C. Room temperature is usually favorable. N-(hydrocarbyl)phosphoric or thiophosphoric triamide precipitates, while the side phospho-products remain in the aromatic phase. Pure solid product is separated by filtration, washed with cold aromatic solvent and dried. The yields of the crude product are about 80% with the purity of about 95%. The major impurity is ammonium chloride. A repeated recrystallization of the crude product from the aromatic solvent provides the product purity of more than 98-99% with the yield of 80-85%. In this application, the % of purity is weight %, if not expressly stated otherwise.

The process according to the present invention can be carried out either as batch production or as continuous process.

Another object of the present invention is N-(hydrocarbyl) phosphoric or thiophosphoric triamide of general formula I $$(RNH)(NH_2)_2P=X \qquad (I)$$

wherein R is a hydrocarbyl group and X is O or S,
having the purity of at least 98%. Preferably, the compound of general formula I is N-(n-butyl)thiophosphoric triamide.

A further object of the present invention is N-(hydrocarbyl) phosphoric or thiophosphoric triamide of general formula I $$(RNH)(NH_2)_2P=X \qquad (I)$$

wherein R is a hydrocarbyl group and X is O or S,
having the purity of at least 99%. Preferably, the compound of general formula I is N-(n-butyl)thiophosphoric triamide.

The invention is further explained in more detail by way of examples. These examples are illustrative only and do not further limit the scope of the invention as defined in the claims and in the description.

EXAMPLES

Analytical methods used:

High-performance liquid chromatography (HPLC): Reverse-phase HPLC, C18 column, mobile phase: methanol-water with the gradient of methanol from 60% w/w to 100% w/w, detection UV (210 nm) and ELSD.

Nuclear magnetic resonance (NMR): $^{31}$P-NMR, resonance frequency 200 MHz, about 5 mg of sample was dissolved in 0.5 ml $CDCl_3$, aqueous 85% phosphoric acid in sealed capillary was used as external standard, $^1$H decoupling of spectrum was used.

Example 1

The process according to this example was carried out in a fume-hood. A 100 ml glass flask equipped with a dosing funnel, a condenser with a liquid stopper with toluene, a magnetic stirrer and a water bath was used.

Solution of 5.0 ml dry n-butylamine, 99% (3.7 g, 50 mmol) in 25 ml dry toluene (molecular sieve type 4A was used for drying toluene) was added to the solution of 2.6 ml $PSCl_3$, 98% (4.34 g, 25 mmol) in 5 ml dry toluene during 1 h with cooling to room temperature (RT). The solid phase containing n-butylammonium chloride was removed from the resulting suspension by filtration, carefully sucked and washed with 10 ml of dry toluene. The combined toluene filtrates were cooled to 0° C. (water with ice bath) and then ammonia was added in ten portions of about 2 ml/portion, one portion every 20 minutes. The resulting suspension was stirred without cooling for additional 1 h, then heated to 65° C. and filtered at this temperature. The hot solution was cooled to RT, stirred for 1 h and the precipitated N-(n-butyl)thiophosphoric triamide (NBPT) was separated by filtration. The crude NBPT was carefully sucked and washed with 10 ml of toluene. The yield of crude NBPT was 3.35 g (80%) with the purity of 96%. Repeated recrystallization of the crude NBPT from toluene (1 g/6 ml, 70° C./20° C.) provided the yield of NBPT of 2.85 g (85.1%) with the purity of >99% ($^{31}$P-NMR, the $^{31}$P chemical shift for NBPT is 59.88 ppm—a singlet after $^1$H-decoupling).

Example 2

The process according to this example was carried out in a fume-hood. A 100 ml glass flask equipped with a dosing funnel, a condenser with a liquid stopper with toluene, a magnetic stirrer and water bath was used for performing the first step of the reaction. A 250 ml stainless steel autoclave equipped with a manometer, a thermometer well, a dosing valve, a releasing valve, a magnetic stirrer and a water bath was used for the second step of the reaction.

Solution of 5.0 ml dry n-butylamine, 99% (3.7 g, 50 mmol) in 25 ml dry toluene was added to the solution of 2.6 ml $PSCl_3$, 98% (4.34 g, 25 mmol) in 5 ml dry toluene during 1 h with cooling to room temperature (RT). Solid phase was removed from the resulting suspension by filtration. The cake was carefully sucked and washed with 10 ml of dry toluene. The combined toluene filtrates were placed into autoclave, which was then closed. The dosing valve was connected to ammonia source. Ammonia was dosed to the vigorously stirred toluene phase in the autoclave at room temperature by maintaining ammonia overpressure at 2 bars. The reaction was finished when no drop of ammonia overpressure was observed for 30 minutes. The product mixture was then heated to 65° C. The conversion was completed and NBPT was dissolved at this temperature. The overpressure was slowly released and the autoclave was opened (this must be performed in a fume-hood). The hot suspension was filtered at the temperature of 65° C. The autoclave and then the cake of ammonium chloride were washed with 20 ml of hot dry toluene. The collected hot filtrates were cooled to RT and stirred for 1 hour. The crude NBPT was carefully sucked and washed with 10 ml of dry toluene. The yield of crude NBPT was 3.5 g (83.7%) with the purity of 96%. Repeated recrystallization of the crude NBPT from toluene (1 g/6 ml, 70° C./20° C.) provided the yield of NBPT of 2.97 g (84.9%) with the purity of >99% ($^{31}$P-NMR).

Example 3

The process of example 2 was repeated, while 4.65 ml of dry aniline, 98% (50 mmol) was used instead of 5.0 ml of dry n-butylamine, 99% (50 mmol). The yield of the crude N-phenylthiophosphoric triamide (hereinafter abbreviated NPPT) was 3.51 g (75%) with the purity of 95%. Repeated recrystallization of the crude NPPT from toluene (1 g/6 ml, 7° C./20° C.) provided the yield of NPPT of 2.74 g (78%) with the purity of >98% (HPLC).

Example 4

The process of example 2 was repeated, while 2.37 ml $POCl_3$, 98% (25 mmol) was used instead of 2.6 ml $PSCl_3$, 98% (25 mmol). The yield of the crude N-(n-butyl)phosphoric triamide (hereinafter abbreviated BPT) was 3.14 g (83.1%) with the purity of 97%. Repeated recrystallization of the crude BPT from toluene (1 g/6 ml, 70° C./20° C.) provided the yield of BPT of 2.67 g (85.0%) with the purity of >99% (HPLC).

Example 5

The solid cake of n-butylammonium chloride from the example 1 was dried. The yield was 2.7 g (24.6 mmol). The ammonium chloride was suspended in 26 ml of toluene and 35 mmol of KOH in the form of 30% aqueous solution was then added to the stirred suspension. The resulting mixture was stirred for 30 minutes at room temperature and then filtered to remove the solid portion of KCl. The toluene phase with n-butylamine was separated from the water phase and dried with about 1 g of solid KOH. Dry toluene phase containing about 24 mmol (calculated approximate yield of the previous step) of n-butylamine was obtained. 2.6 ml of fresh n-butylamine, 99% (26 mmol) was added to the toluene phase to obtain the final solution of about 50 mmol (calculated yield) of n-butylamine in 25 ml toluene. This n-butylamine solution in toluene was used for preparing NBPT according to example 1. The yield of crude NBPT was 3.3 g (78.9%) with the purity of 95%. Repeated recrystallization of the crude NBPT from toluene (1 g/6 ml, 70° C./20° C.) provided the yield of NBPT of 2.77 g (84.0%) with the purity of >99% (HPLC).

Example 6

This example shows the process of the present invention on a pilot scale.

a) Preparation of N-(n-butyl)amidethiophosphoryl dichloride ($NBPCl_2$)

In a 4-liter sulfonation flask equipped with a mechanical stirrer, a thermometer, a dosing funnel with a calcium chloride stopper and placed in a cold water bath (0° C.), 347 g (2.05 mol) of thiophosphoryl chloride and 800 ml of dry toluene (water content≦500 ppm) were brought into reaction. The mixture was vigorously stirred and cooled to ca 10° C. and 299.6 g (4.10 mol) of n-butylamine in 1200 ml of dry toluene (water content≦500 ppm) was added dropwise from the dosing funnel during 60 minutes. The reaction temperature was maintained in the range of from 15 to 20° C. After adding all the n-butylamine solution, the mixture was cooled to 2° C. at stirring. The resulting suspension was filtered and the filtration cake of n-butylammonium chloride was washed with 250 ml of cold dry toluene (2° C.) and thoroughly sucked. Almost quantitative yield of $NBPCl_2$ toluene solution having the volume of 2250 ml was obtained, which was immediately used for the following preparation of N-(n-butyl)thiophosphoric triamide.

b) Preparation of N-(n-butyl)thiophosphoric triamide (NBPT)

Into a 4-liter sulfonation flask equipped with a mechanical stirrer, a thermometer, a dosing funnel with a calcium chloride stopper and cooled to the temperature of −40° C., 300 ml of dry toluene (water content≦500 ppm) and 15 equivalents of liquid ammonia (30 mol) were poured. 2250 ml of cooled (−17 ° C.) $NBPCl_2$ solution obtained in the previous step was added at cooling and stirring by such a rate that the temperature of the reaction mixture does not rise over −18 ° C. After all the $NBPCl_2$ toluene solution was added, cooling of the reaction mixture was ceased and the resulting suspension was stirred for 1 hour without any tempering. During another 1 hour, the suspension was warmed to the room temperature, and during one more hour, the suspension was heated to 65-70° C. A fume hood is recommended. After 30 minutes, the suspension was heat-filtered. The filtration cake of $NH_4Cl$ was washed with 50 ml of hot toluene (70° C.). The combined toluene filtrates were cooled to 3-5° C., the resulting product suspension was stirred for 3 hours and then filtered. The filtration cake of the product was washed with 50 ml of cold toluene (3-5° C.), thoroughly sucked, dried, weighed and analysed. 234.0 g of white crystalline product NBPT (70% of the calculated yield) was obtained, with the purity of 97.0% (HPLC). A purity of NBPT greater than 99.0% was achieved by simple re-crystallization from toluene.

The invention calimed is:

1. A process for preparing N-(hydrocarbyl)phosphoric or thiophosphoric triamide of general formula I (RNH)(NH$_2$)$_2$P=X (I)

wherein R is a hydrocarbyl group and X is O or S, characterized in that it comprises the steps of:
a) reacting about one equivalent of Cl$_3$P=X, wherein X is O or S, with about two equivalents of hydrocarbylamine in an aromatic solvent to obtain a solution of a compound of general formula II (RNH)Cl$_2$P=X (II)

wherein R and X are as defined above, and a solid phase containing
hydrocarbylammonium chloride,
b) removing the solid phase to obtain the solution,
c) adding at least four equivalents of ammonia to the solution obtained in step b) to obtain a suspension of solid compound of general formula I and solid ammonium chloride in the aromatic solvent,
d) heating the suspension obtained in step c) to the temperature in the range of from 50 to 80° C. to obtain a solution of the compound of general formula I and a solid phase containing ammonium chloride,
e) removing the solid phase at the temperature in the range of from 50 to 80° C. to obtain the solution,
f) cooling the solution obtained in step e) to the temperature in the range of from 0 to 25° C. to obtain solid product of the general formula I.

2. The process according to claim 1, wherein the hydrocarbylamine is n-butylamine and R is n-butyl.

3. The process according to claim 1, wherein the solid phase obtained in step b) is treated with alkali metal hydroxide and the thus obtained hydrocarbylamine is re-used in step a) of the process.

4. The process according to claim 1, wherein the aromatic solvent is toluene.

5. The process according to claim 1, further comprising recrystalizing the product of step f) from aromatic solvent, and
providing product of the general formula I having a purity of not less than 98% by weight.

6. The process according to claim 1, further comprising recrystalizing the product of step f) from aromatic solvent, and
providing product of the general formula I having a purity of not less than 99% by weight.

7. The process according to claim 4, further comprising recrystalizing the product of step f) from aromatic solvent, and
providing product of the general formula I having a purity of not less than 98% by weight.

8. The process according to claim 4, further comprising recrystalizing the product of step f) from aromatic solvent, and
providing product of the general formula I having a purity of not less than 99% by weight.

* * * * *